US00PP16209P3

(12) United States Plant Patent

Miyazaki et al.

(10) Patent No.: US PP16,209 P3
(45) Date of Patent: Jan. 24, 2006

(54) *PETUNIA* PLANT NAMED 'SUNBABUVE'

(50) Latin Name: *Petunia hybrida*
Varietal Denomination: Sunbabuve

(75) Inventors: Kiyoshi Miyazaki, Hikone (JP); Kazunari Iwaki, Omihachiman (JP); Takuro Ishihara, Higashikurume (JP)

(73) Assignee: Suntory Flowers Limited, Tokyo (JP)

( * ) Notice: Subject to any disclaimer, the term of this patent is extended or adjusted under 35 U.S.C. 154(b) by 80 days.

(21) Appl. No.: 10/812,864

(22) Filed: Mar. 29, 2004

(65) Prior Publication Data

US 2005/0217001 P1 Sep. 29, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

| | | | | |
|---|---|---|---|---|
| PP6,899 P | | 7/1989 | Tsuda et al. | |
| PP6,914 P | | 7/1989 | Tsuda et al. | |
| PP6,915 P | | 7/1989 | Tsuda et al. | |
| PP9,322 P | | 10/1995 | Tachibana et al. | |
| PP13,543 P2 | * | 2/2003 | Sakazaki | Plt./356 |

FOREIGN PATENT DOCUMENTS

| | | |
|---|---|---|
| JP | PBR 4011 | 3/1994 |
| JP | PBR 8036 | 3/2000 |

OTHER PUBLICATIONS

Surfinia Europe's Most Popular Petunia http://www.surfinia.com/2003/surfinia.html.*

2003 New Varieties Petunia http://www.greenbeam.com/features/tour0609031.stm Jun. 9, 2003.*

Suntory: Petunia Baby Blue Veined http://www.dupontnursery.com/Product.aspx?cid=3&pid=59.*

UPOV ROM GTITM Computer Database, GTI Jouve Retrieval Software 2004/06 Citation for Sunbabuve.*

Germania Seed Homepage http://www.germaniaseed.com.*

Suntory Collection and Other Specialty Annuals http://www.germaniaseed.com/pdf/04–747Pineae.pdf Jul. 1, 2003.*

Explanation of Publications of Japanese PBR Registration.

Suntory Flowers Ltd., "Flower & Green, the newest catalog 2004" Published 2003, (Explanation for IDS Document).

Jackson & Perkins wholesale, Inc., U.S.A., "The 2004 Suntory Collection" Published 2003, (Explanation for IDS Document).

Pineae Greenhouses, Inc., U.S.A., "Pineae Peak Performers featuring the 2004 Suntory Collection" Published 2003, (Explanation for IDS Document).

Moerheim New Plant bv., NL, "Suntory Collection 2004" Published 2003, (Explanation for IDS Document).

Ramm Botanicals Pty Ltd., AU, "Colour Wave Collection 2003–4 . . . beautiful flowering plants" Published 2002, (Explanation for IDS Document).

* cited by examiner

*Primary Examiner*—Kent Bell
*Assistant Examiner*—W. C. Haas
(74) *Attorney, Agent, or Firm*—Christie, Parker and Hale, LLP

(57) ABSTRACT

Disclosed herein is a new and distinct variety of *Petunia* plant having a decumbent habit and long, spindly stems. The *Petunia* plant has abundant branching, and a great profusion of blooms, the whole plant remaining in bloom for a considerable period of time. The flowers are single and small, the petals having a very pale purple color with vivid purple vein. The inside color of the corolla throat is brilliant purple and the outside of the corolla tube is light purple. The plant exhibits high resistance to rain, heat, cold and disease.

2 Drawing Sheets

Botanical designation: *Petunia hybrida*.
Variety denomination: 'Sunbabuve'.

BACKGROUND OF THE VARIETY

The present invention relates to a new and distinct variety of *Petunia* plant originated from crossing of a wild type *Petunia* plant called 'NW-4' as the female parent and a seedling of *Petunia* plant called 'Dbl.BV' as the male parent.

The *Petunia* is a very popular plant that is used for flower bedding and potting in the summer season. There are only a few *Petunia* varieties known to the inventors which do not have an upright growth habit and which have a high resistance to rain, heat, and disease. These *petunia* plants, such as the Revolution series cultivars 'Revolution Purplepink' (U.S. Plant Pat. No. 6,915), 'Revolution Brilliantpink' (U.S. Plant Pat. No. 6,914), 'Revolution Brilliantpink-mini' (U.S. Plant Pat. No. 6,899), and 'Revolution Bluevein' (U.S. Plant Pat. No. 9,322) are decumbent type plants having long stems, a lower plant height, abundant branching, and a high resistance to heat, rain and disease. However, there are only a few *Petunia* varieties having a great profusion of small size flowers, pale purple color with vein patterned flower petals and a high resistance to rain, heat, and disease known to the inventors. Accordingly, this invention was aimed at obtaining a new variety having purplish white colored petals with vivid violet vein, together with the above features.

The female parent 'NW-4' (unpatented) used in the crossing that created 'Sunbabuve' is a wild type *Petunia* plant native to Brazil, having a decumbent habit with long stems and many branches. The leaf is very small without petiole. It has very small single flowers, the petals having yellowish white (R.H.S. 155B) with strong purplish pink (R.H.S. 84A) vein.

The male parent 'Dbl.BV' (non-patented) used in the crossing that created 'Sunbabuve' is a strain of our breeding lines 'Dbl.BV' has an erect growth habit with many branches and large double flowers. The petals have a violet blue (R.H.S. N89A) color without vein.

In April 1998, crossing of 'NW-4' as the female parent and 'Dbl.BV' as the pollen parent was conducted at Yokaichi-shi, Shiga-ken, Japan. In January 1999, 120 seedlings were obtained from that crossing. These seedlings were grown in pots in glasshouses and were evaluated. One seedling was selected in view of its decumbent growth habit, flower size and color. That seedling was propagated by cuttings from July 1999, and was the subject of a trial carried out by flower potting and bedding from April 2000. The botanical characteristics of that plant were then examined, using similar varieties 'Revolution Bluevein' and 'Revolution violet-mini' (unpatented) for comparison. As a result, it was concluded that this *Petunia* plant is distinguishable from any other variety, whose existence is known to us, and is uniform and stable in its characteristics. Then the new variety of *Petunia* plant was named 'Sunbabuve'.

In the following description, the color-cording is in accordance with The R.H.S. Colour Chart.

SUMMARY OF THE VARIETY

This new variety is unlike any *Petunia* commercially available, known to the inventors, as evidenced by the following unique combinations of characteristics.

1. Decumbent growth habit with long, spindly stems.
2. Having abundant branching and a great profusion of blooms.
3. The flowers are single and small. The petal color is very pale purple (R.H.S. 92D) with vivid purple (R.H.S. N87A) vein.
4. The plant has a high resistance to rain, cold, heat and disease.

The new variety 'Sunbabuve' differs from the similar variety 'Revolution Bluevein' in the following points.

1. The stem of 'Sunbabuve' is thinner than that of 'Revolution Bluevein'.
2. The flower diameter of 'Sunbabuve' is smaller than that of 'Revolution Bluevein'.
3. The petal color of 'Sunbabuve' is very pale purple (R.H.S. 92D) with vivid purple (R.H.S. N87A) vein. That of 'Revolution Bluevein' is very pale purple (R.H.S. 91C) with moderate purple (R.H.S. 83A) vein.
4. The peduncle of 'Sunbabuve' is shorter than that of 'Revolution Bluevein'.
5. The peduncle of 'Sunbabuve' is thinner than that of 'Revolution Bluevein'.

The new variety 'Sunbabuve' differs from the similar variety 'Revolution violet-mini' in the following points.

1. The leaf of 'Sunbabuve' is smaller than that of 'Revolution violet-mini'.
2. The flower diameter of 'Sunbabuve' is smaller than that of 'Revolution violet-mini'.
3. The petal color of 'Sunbabuve' is very pale purple (R.H.S. 92D) with vivid purple (R.H.S. N87A) vein. That of 'Revolution violet-mini' is vivid purple (R.H.S. N81A) without vein.
4. The apex shape of petal of 'Sunbabuve' is rounded. That of 'Revolution violet-mini' is obtuse.
5. Flowering time of 'Sunbabuve' is earlier than that of 'Revolution violet-mini'.

The new variety of *Petunia* plant 'Sunbabuve' was asexually reproduced by the use of cuttings at Yokaichi-shi, Shiga-ken, Japan, and the homogeneity and stability thereof were confirmed. The instant variety retains its distinctive characteristics and reproduces true to type in successive generations.

BRIEF DESCRIPTION OF THE PHOTOGRAPH

The depicted plants had been reproduced by the use of cuttings and were photographed during July 2002 while growing outdoors in 20 cm pots at an age of approximately 6 months at Yokaichi-shi, Shiga-ken, Japan.

DESCRIPTION OF THE VARIETY

Figure 1:
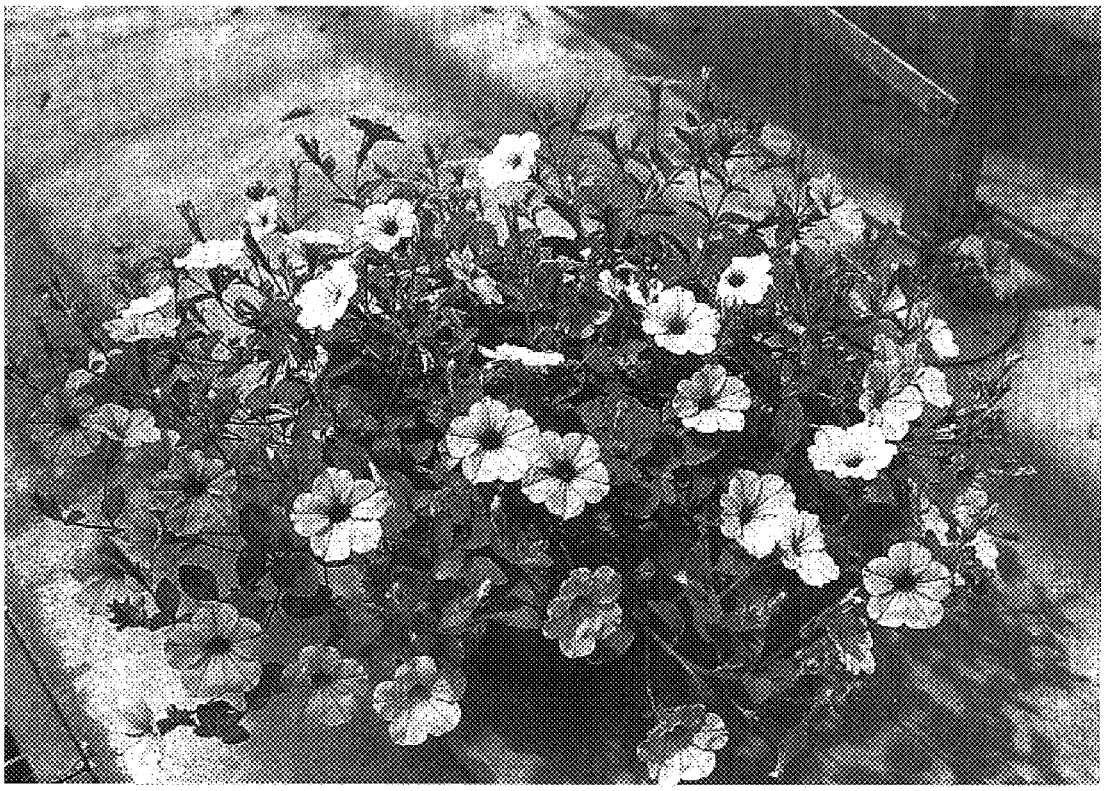
Fig. 1 illustrates a typical plant of the new variety of *Petunia* plant 'Sunbabuve' while growing in a pot.
Figure 2:
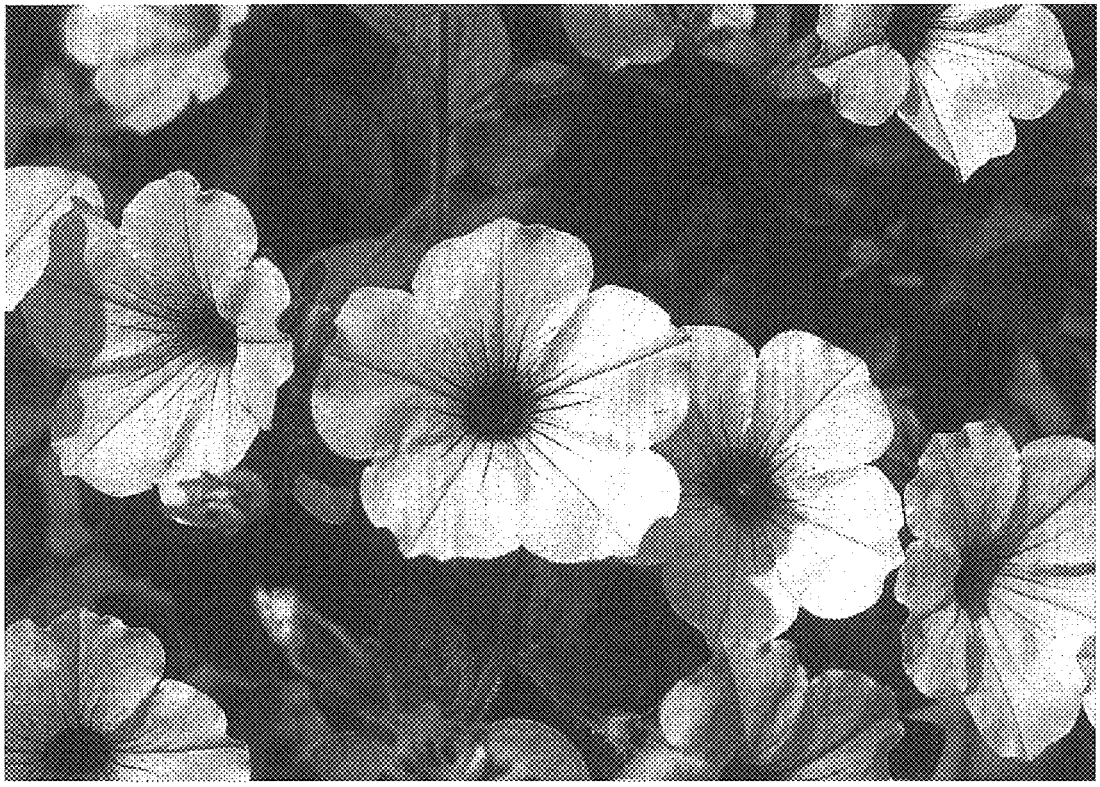
Fig. 2 illustrates a close view of typical foliage and blossoms of the new variety of *Petunia* plant 'Sunbabuve'.

The botanical characteristics of the new and distinct variety of *Petunia* plant named 'Sunbavube' are as follows when observed as grown in typical outdoor conditions during August at Yokaichi-shi, Shiga-ken, Japan, at an age of approximately 7 months. The average day temperature is approximately 23° C. and the average night temperature is approximately 15° C.

Plant:

*Growth habit.*—Decumbent.
*Plant height.*—Approximately 19 cm.
*Spreading area of plant.*—Approximately 85 cm.
*Booming period.*—Early April to late October in the southern Kanto area, Japan. The plant shape does not change throughout this period. A typical flower commonly lasts approximately 5 days on the plant when experiencing a temperature of approximately 20° C.

Stem:

*Length.*—Approximately 14 cm.
*Diameter.*—Approximately 2.2 mm.
*Pubescence.*—Present and typical of the species.
*Branching.*—Approximately 20 branches per plant.
*Internode length.*—Approximately 3.0 cm.
*Color.*—R.H.S. 145C (Light yellow green).

Leaf:

*Whole shape.*—Elliptic. The apex shape is acute, and the base shape is attenuate.
*Length.*—Approximately 4.2 cm.
*Width.*—Approximately 2.6 cm.
*Color.*—Upper side color is R.H.S. 147B (moderate yellow green). Lower side color is R.H.S. 137C (moderate yellow green).
*Thickness.*—Approximately 0.9 mm.
*Pubescence.*—Sparse.

Flower:

*Facing direction.*—Slanted upward.
*Type.*—Single.
*Shape.*—Funnel-shaped, with five-fissures.
*Shape of petal tip.*—Round.

*Lobation*.—Shallow.

*Waving of petal*.—Weak.

*Flower diameter*.—Approximately 4.0 cm.

*Flower depth*.—Approximately 3.0 cm.

*Flower color*.—Upper Petal Surface Color: near R.H.S. 92D with R.H.S. N87A veins. Lower Petal Surface Color: near R.H.S. 92D with R.H.S. N87A veins. Inside color of flower throat: R.H.S. 86D. Outside color of flower tube: R.H.S. 81D.

*Calyx*.—Narrow, 5 sepals fused at the base. Diameter: Approximately 15 mm. Depth: Approximately 10 mm. Color (upper and lower surfaces): near R.H.S. 147B. Texture (both surfaces): Smooth.

*Reproductive organs*.—1 normal pistil and 5 normal stamens. Color of pistil is R.H.S. 144B (vivid yellow green). Color of stamen is R.H.S. 79D (moderate reddish purple).

*Peduncle*.—Diameter: Approximately 0.7 mm. Length: Approximately 1.2 cm. Color: near R.H.S. 145C. Texture: Smooth.

*Physiological and ecological characteristics*.—High resistance to rain, cold, heat and disease. Moderate resistance to pests. 'Sunbabuve' has a low temperature tolerance of at least 5° C.

Seed production has not been observed.

This new variety of *Petunia* plant is most suitable for flower bedding and potting, particularly in hanging pots or planters, and is excellent for use as ground cover. Pinching of old blossoms will enhance the formation of new blossoms.

It is claimed:

1. A new and distinct variety of *Petunia* plant named 'Sunbabuve', substantially as herein illustrated and described.

* * * * *